United States Patent
Haupt Jabri et al.

(10) Patent No.: US 9,492,350 B2
(45) Date of Patent: Nov. 15, 2016

(54) DIALYSIS BAG WITH ANTI-OCCLUSION FEATURE

(71) Applicants: BAXTER INTERNATIONAL INC., Deerfield, IL (US); BAXTER HEALTHCARE S.A., Glattpark (Opfikon) (CH)

(72) Inventors: Nicole Michaela Haupt Jabri, Oak Creek, WI (US); Robin Gail Pauley, Lake Villa, IL (US); Brian Richard Micheli, Lindenhurst, IL (US); Lewis E. Daniels, Jr., Wonder Lake, IL (US); James Patrick Condon, Hebron, IL (US); Gert Najdeni, Chicago, IL (US); Mack David Elliott, Marion, NC (US)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 334 days.

(21) Appl. No.: 13/826,763

(22) Filed: Mar. 14, 2013

(65) Prior Publication Data

US 2014/0276528 A1 Sep. 18, 2014

(51) Int. Cl.
*A61B 19/00* (2006.01)
*A61J 1/10* (2006.01)
*A61J 1/14* (2006.01)
(Continued)

(52) U.S. Cl.
CPC ............. *A61J 1/10* (2013.01); *A61J 1/1475* (2013.01); *A61J 1/1493* (2013.01); *A61M 1/1668* (2014.02); *B32B 1/00* (2013.01); *B32B 27/08* (2013.01); *B32B 27/304* (2013.01); *A61J 1/2075* (2015.05); *A61J 2200/76* (2013.01); *A61M 1/167* (2014.02); *A61M 1/1656* (2013.01); *B32B 2439/46* (2013.01); *B65D 77/065* (2013.01); *B65D 2231/002* (2013.01); *Y10S 128/24* (2013.01)

(58) Field of Classification Search
CPC ........ A61J 1/10; A61J 2200/76; A61J 1/143; A61J 2001/2075; A61J 1/1475; A61M 1/1668; A61M 1/167; A61M 1/1656; B32B 1/00; B65D 2231/002; B65D 77/065; Y10S 128/24
USPC ....................................................... 604/408
See application file for complete search history.

(56) References Cited

U.S. PATENT DOCUMENTS

| | | |
|---|---|---|
| 2,954,768 A | 10/1960 | Hamilton |
| 3,064,652 A | 11/1962 | Corcoran et al. |

(Continued)

FOREIGN PATENT DOCUMENTS

| | | |
|---|---|---|
| DE | 3803776 | 8/1989 |
| WO | 84/02648 | 7/1984 |

*Primary Examiner* — Tatyana Zalukaeva
*Assistant Examiner* — Andrew J Mensh
(74) *Attorney, Agent, or Firm* — Greer, Burns & Crain, Ltd.

(57) ABSTRACT

A dialysis bag is provided, including a first layer of film and a second layer of film each having a closed end and an opposite outlet end, the layers sealed together about corresponding peripheral edges to define a bag chamber. An outlet assembly is sealingly disposed at the corresponding outlet ends and has a tubular administrative outlet with an inlet and is in fluid communication with the bag chamber. A dimple is formed in at least one of the layers adjacent to the inlet for preventing occlusion as a fluid level decreases in the bag.

17 Claims, 5 Drawing Sheets

(51) Int. Cl.
  *B32B 1/00* (2006.01)
  *B32B 27/08* (2006.01)
  *B32B 27/30* (2006.01)
  *A61M 1/16* (2006.01)
  *B65D 77/06* (2006.01)

(56) References Cited

U.S. PATENT DOCUMENTS

| | | |
|---|---|---|
| 3,081,911 A | 3/1963 | Scholle |
| 3,240,399 A | 3/1966 | Frandeen |
| 3,420,413 A | 1/1969 | Corsette |
| 3,831,814 A | 8/1974 | Butler |
| 4,096,897 A | 6/1978 | Cammarata, III |
| 4,159,790 A | 7/1979 | Bailey |
| 4,308,904 A | 1/1982 | Martin et al. |
| 4,381,846 A | 5/1983 | Heck |
| 4,479,989 A | 10/1984 | Mahal |
| 4,596,573 A | 6/1986 | Donnan et al. |
| 4,601,410 A | 7/1986 | Bond |
| 4,785,859 A | 11/1988 | Gustavsson et al. |
| 4,893,731 A * | 1/1990 | Richter .............. 222/92 |
| 5,071,413 A | 12/1991 | Utterberg |
| 5,108,387 A | 4/1992 | Falk et al. |
| 5,312,189 A * | 5/1994 | Aeschbach ........ B65D 75/5822 383/207 |
| 5,391,163 A | 2/1995 | Christine et al. |
| 5,405,333 A | 4/1995 | Richmond |
| 5,573,526 A | 11/1996 | Hess |
| 5,647,511 A | 7/1997 | Bond |
| 5,728,086 A * | 3/1998 | Niedospial, Jr. .......... A61J 1/10 604/262 |
| 5,728,087 A | 3/1998 | Niedospial, Jr. |
| 5,738,671 A | 4/1998 | Niedospial, Jr. et al. |
| 5,779,693 A | 7/1998 | Ropiak et al. |
| 5,934,345 A | 8/1999 | Moynihan et al. |
| 5,941,421 A | 8/1999 | Overman et al. |
| 5,941,866 A * | 8/1999 | Niedospial, Jr. .............. 604/408 |
| 6,068,617 A | 5/2000 | Richmond |
| 6,098,673 A | 8/2000 | Moynihan et al. |
| 6,102,252 A | 8/2000 | Overman et al. |
| 6,179,823 B1 | 1/2001 | Niedospial, Jr. |
| 6,607,097 B2 | 8/2003 | Savage et al. |
| 6,695,829 B2 | 2/2004 | Hellstrom et al. |
| 6,715,644 B2 | 4/2004 | Wilford |
| 6,848,596 B2 | 2/2005 | Balz et al. |
| 6,851,579 B2 | 2/2005 | Savage et al. |
| 6,984,278 B2 | 1/2006 | Anderson et al. |
| 7,017,781 B2 * | 3/2006 | Provenza ................... 222/105 |
| 7,357,276 B2 | 4/2008 | Savage et al. |
| 8,231,596 B2 | 7/2012 | Okiyama |
| 2004/0243094 A1 | 12/2004 | Dumon D'Ayot et al. |
| 2006/0043012 A1 | 3/2006 | Ritter |
| 2008/0149668 A1 | 6/2008 | Johnson et al. |
| 2010/0102080 A1 | 4/2010 | Johnson et al. |
| 2010/0228196 A1 | 9/2010 | Wyss |
| 2012/0136304 A1 | 5/2012 | Wyss et al. |

\* cited by examiner

DIALYSIS BAG WITH ANTI-OCCLUSION FEATURE

BACKGROUND

The present invention relates generally to bags designed for dispensing medical fluids, and particularly to an improved dialysis bag having features for preventing occlusion or flow choke-off of the outlet port.

Patients suffering from certain forms of chronic kidney disease are treated with peritoneal dialysis, which can be performed at home. Such treatment involves periodically flushing the peritoneal cavity in the abdomen with a remedial fluid that absorbs unwanted electrolytes, urea, glucose, albumin and other small molecules that are filtered by the kidneys in a healthy individual. Upon flushing the fluid from the peritoneal cavity, the unwanted substances are removed from the body. In this manner, a patient can avoid the inconvenience and relatively more drastic swings in levels of unwanted substances common when conventional dialysis is used.

As part of the home dialysis procedure, a bag of sterilized peritoneal fluid is laid on its side in a horizontal orientation upon a heated surface of a computerized fluid pumping device, exemplified by the Baxter HomeChoice Automated Peritoneal Dialysis (APD) System. Additional supply bags normally connected by a tubing set with the heated bag may also be laid on their sides in close proximity to the pumping device when higher volumes of dialysis fluid are prescribed for treatment. In operation, a bag lies flat upon the heated upper surface of the APD cycler or device. A tubular administrative outlet of the bag is placed in fluid communication with the disposable APD tubing set, and fluid is pumped into the patient according to a pre-selected dosing regimen. It is common for a peritoneal flushing treatment using an APD to last as long as 8 hours. During this treatment, at least one and often several large volume bags of dialysis fluid are used. The volumes of these bags may range between 2000 ml and 6000 ml.

In some cases, it has been found that as the bag empties, an upper film of the bag collapses upon an inlet of the outlet tube, thus blocking further flow of fluid to the patient. The APD system is designed to generate an alarm in such instances, as well as in other situations when fluid flow falls below preset levels. However, due to patient inconvenience and the unwanted interruption in the treatment program, such alarms are to be avoided.

SUMMARY

The above-identified problem of unwanted dialysis bag occlusion is met by the present peritoneal dialysis bag, which features a dimple, fold, wrinkle or crease (referred to in the application as a dimple) positioned in one of the film layers forming the bag, near an inlet of the outlet tube. In the preferred embodiment, the dimple is constructed and arranged for maintaining a space around the inlet that separates it from the adjacent bag film regardless of the relative angular position of the tube, and regardless of the amount of fluid remaining in the bag. Creation of the dimple is achieved by a combination of formations, including an outlet end bag seal that is formed asymmetrically, such that the fold is created in close proximity to the inlet for preventing occlusion. In addition, the outlet end bag seal is provided with structural ribs for enhancing the formation of the dimple. Also, the inlet tube itself is located closer to the outlet end bag seal than in conventional dialysis bags. Furthermore, the outlet end bag seal is separated from an outlet edge of the bag by a sealed web. In a preferred embodiment, the outlet end bag seal has a portion angled to form a 90 degree angle, and is located in close proximity to the tubular administrative outlet. The precise combination of such features may vary to suit the application, provided that the desired dimple is created, and occlusion prevented.

More specifically, a peritoneal dialysis bag is provided, including a bag chamber defined by a pair of complementary films sealed together to form the bag chamber therebetween and having a first, outlet end and a second, closed end opposite the outlet end. The bag layers are sealed together in part at the outlet end by a first outlet end seal. At least one tubular administrative outlet is sealingly disposed at the outlet end and in fluid communication with the bag chamber. A dimple is formed in at least one of the films about an inlet of the outlet for preventing occlusion of the inlet as the bag is depleted of fluid. In some embodiments the dimple extends between and the inlet and the first outlet end seal.

DETAILED DESCRIPTION

Figure 1:
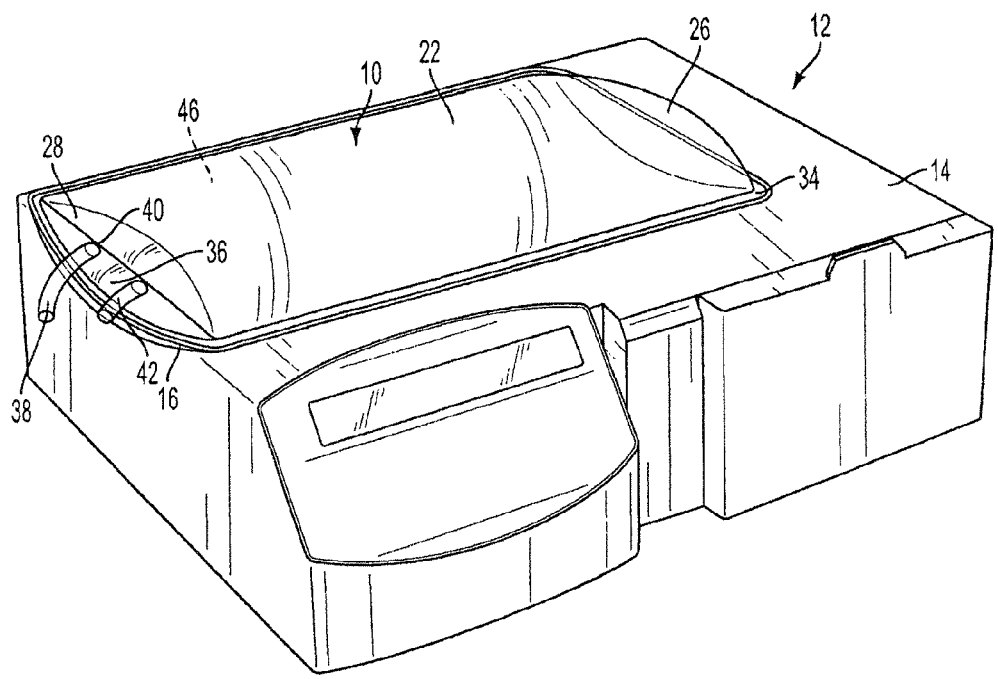
FIG. 1 is a top perspective view of the present dialysis bag operationally disposed upon an APD cycler.

Referring to FIG. 1, the present dialysis bag is generally designated 10 and is shown depicted on an automated peritoneal dialysis system unit, generally designated 12. The unit 12 is depicted as a Baxter HomeChoice APD cycler or unit, however the present bag 10 is contemplated as being suitable for use with other APD cyclers known in the art. Included on the unit 12 is an upper surface 14 forming a generally-concave depression or recess 16 defining a seat for the bag 10 when filled with dialysis fluid, as shown in FIG. 1. The operation of the cycler 12 is well known in the art, and need not be described further.

Figure 2:
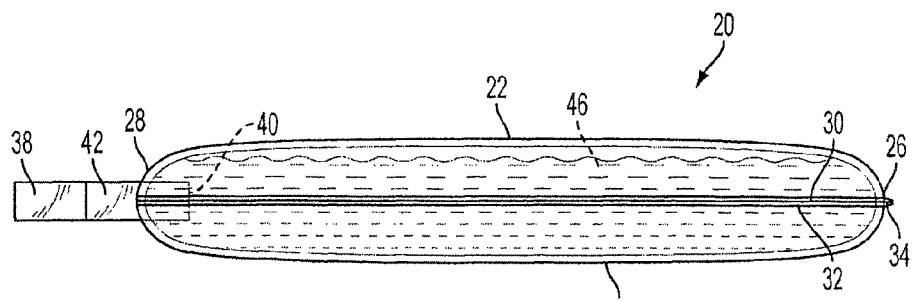
FIG. 2 is a side elevation of a prior art dialysis bag when filled with fluid.
Figure 3:
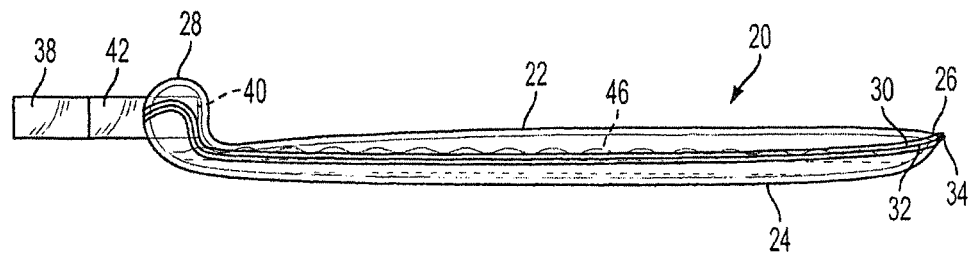
FIG. 3 is a side elevation of the prior art bag of FIG. 2 shown almost empty of fluid with a tubular administrative outlet extending in general alignment with the bag and showing an upper film of the bag causing occlusion of the tubing inlet.
Figure 3A:
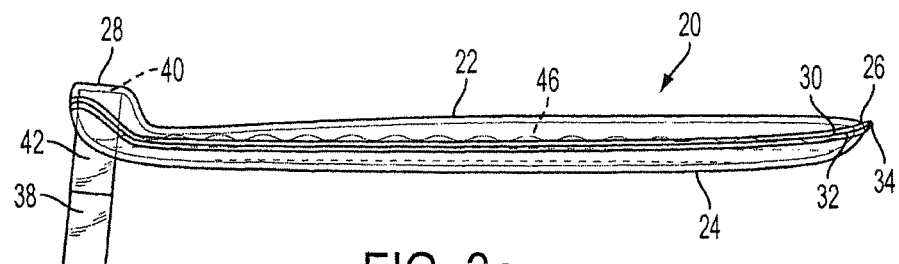
FIG. 3a is a side elevation of the prior art bag of FIG. 2 shown almost empty of fluid with a tubular administrative outlet extending at a distinct downward angle relative to the orientation of the bag and showing an upper film of the bag causing occlusion of the tubing inlet.

Referring now to FIGS. 2, 3 and 3a, a prior art dialysis bag is generally designated 20. Shared components of the bags 10 and 20 are designated with identical reference numbers. A first layer of film 22 and a second layer of film 24, each being made of preferably durable, flexible, thermoformable plastic film such as PVC or the like, are provided, each having a closed end 26 and an opposite outlet end 28. As is well known in the bag manufacturing art, the first and second layers, 22, 24 are joined together along complementary peripheral edges 30, 32 by a peripheral seal 34, conventionally produced by heat sealing, but other known fastening technologies are contemplated.

At the outlet end 28, an outlet assembly 36 (FIG. 1) includes a tubular administrative outlet 38 having an inlet 40, and a supplemental tubular port 42 connected by a web-like outlet seal 44 (FIG. 4) are disposed. Joining the first and second film layers 22, 24 creates an interior bag chamber 46, and the tubular administrative outlet 38 is in fluid communication with the bag chamber. In the case of both bags 10, 20, the interior bag chamber 46 is dimensioned to hold as much as 6300 ml of dialysis fluid. Such bags are referred to in the industry as 6000 ml bags. Other bags of higher or lower volume are also contemplated.

Referring now to FIGS. 4-7, a feature of the present bag 10 is that a dimple 50 is formed in at least the first film layer 22 adjacent to the inlet 40 for preventing occlusion as a fluid level in the bag decreases. The dimple 50 is preferably formed as a fold, wrinkle or small crease in at least the upper film layer 22 that defines an air space 52 (best seen in FIG. 6) above the inlet 40 that remains open regardless of the position of the tubular administrative outlet 38, and regardless of the level of dialysis fluid in the bag 10. It is contemplated that the dimple 50 is formable in either or both of the film layers 22, 24.

Figure 4:
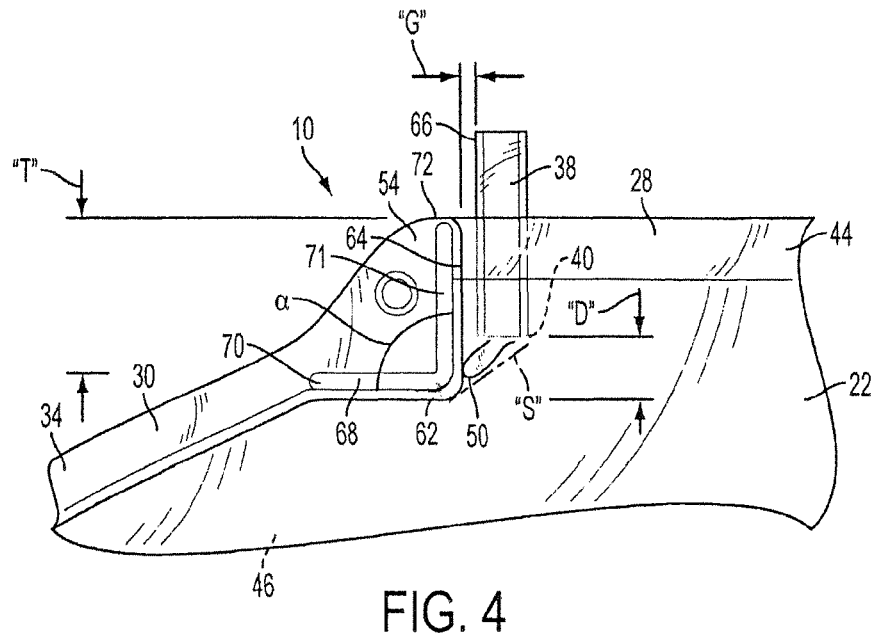
FIG. 4 is a fragmentary overhead plan view of the present dialysis bag.
Figure 7:
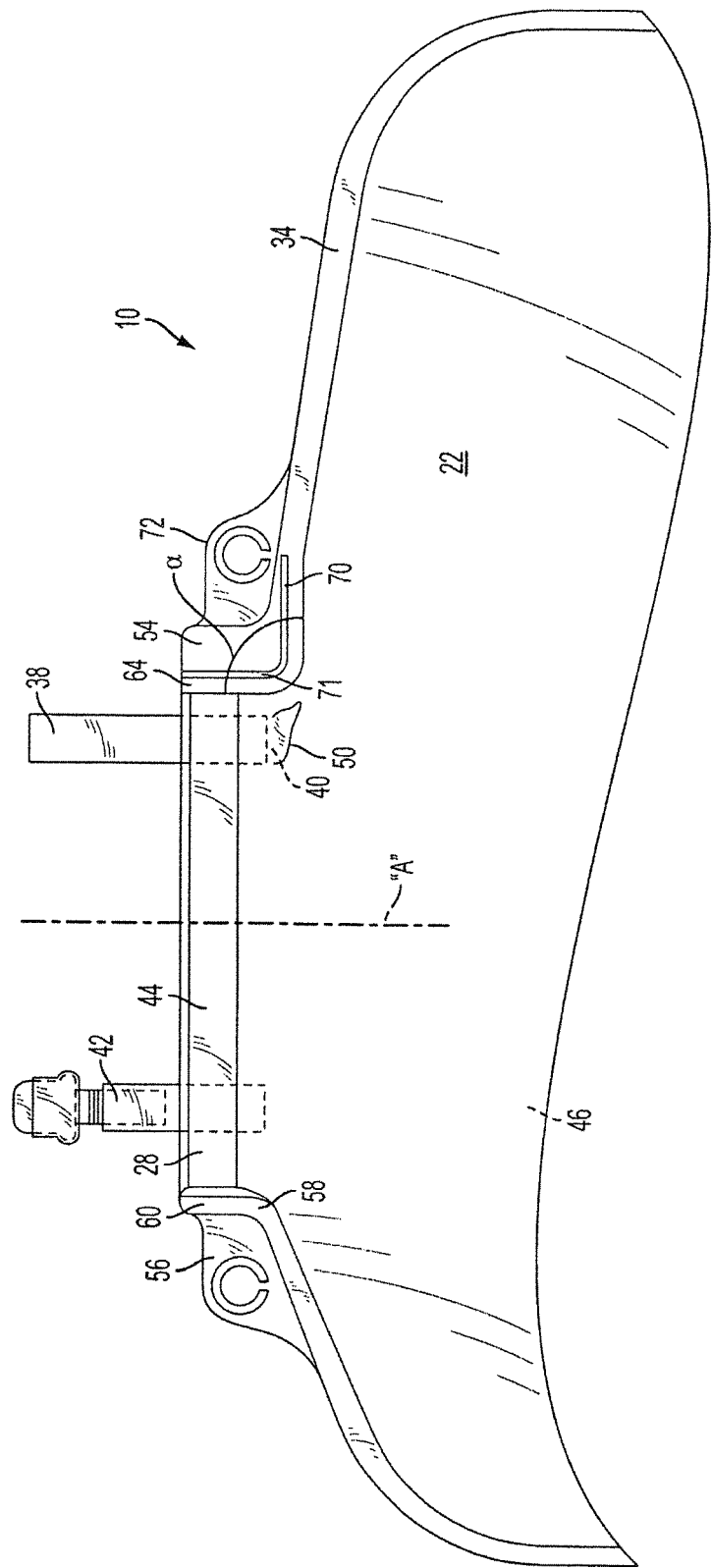
FIG. 7 is an enlarged fragmentary top view of the present bag.

Referring now to FIGS. 4 and 7, a variety of structural features are provided to the bag 10 for creating and/or enhancing the location and performance of the dimple 50. One of such features is the fact that at the outlet end 28, there is an asymmetry of the outlet seal 44. More specifically, a first outlet end seal 54 is distinct from a second outlet end seal 56, such that the outlet end seals are asymmetrical about a longitudinal axis "A" of the bag 10 when viewed from above as seen in FIG. 7. In the preferred embodiment, the dimple 50 is formed closely adjacent the first outlet end seal 54. While in FIG. 4, the first outlet end seal 54 is shown on the left, and in FIG. 7 on the right, it will be appreciated that the seal 54 is locatable at either side of the outlet end 28, depending on the orientation of the bag 10 relative to the APD cycler unit 12, among other things.

Referring now to FIG. 7, as part of the above-described asymmetry, the inlet 40 of the tubular administrative outlet 38 is closer to the first outlet end seal 54 than the second supplemental tubular port 42 is to the second outlet end seal 56. Also, the inlet 40 is closer to the first outlet end seal 54 than to the second outlet seal 56. In addition, it will be seen that at the second outlet end seal 56, an end 58 of an axially-extending segment 60 of the seal 44 is approximately co-linear or horizontally aligned with the inlet 40 of the tubular administrative outlet 38. However, at the first outlet end seal 54, (FIG. 4), a displacement "D" of approximately 3/16 (0.1875) to 9/16 (0.5625) inch is preferably defined between the inlet 40 and an end 62 of the corresponding axially extending seal segment 64. While preferred dimensions of the displacement "D" are provided above, it will be appreciated that other distances are contemplated depending on the application, an insertion depth of the tubular administrative outlet 38 into the chamber 46, and the length of the seal segment 64.

Referring again to FIG. 4, another structural feature that impacts the formation of the dimple 50 is that a gap "G" is defined between the axially-extending seal segment 64 and a closely adjacent peripheral edge 66 of the tubular administrative outlet 38. It is preferred that the gap "G" is approximately 5/16 (0.313) to 1/16 (0.0625) inch and preferably 1/8 (0.125) inch, however other distances are contemplated depending on the application. A preferred location of the dimple 50 is along a line "S" extending generally between the inlet 40 and the end 62, or between the inlet and the first outlet end seal 54. The preferred gap "G" is considered to prevent the formation of pinholes in the creation of the outlet seal 44, which in some cases result in leaks in the bag.

Still another feature of the bag 10 which facilitates the creation of the dimple 50 is a generally "L"-shaped reinforcing rib 68 which includes a transversely extending segment 70 and a segment 71 extending generally parallel to the administrative outlet 38 to define an approximate right angle. A preferred length of the segment 64, extending from the transverse segment 70 to an upper end of the interior chamber 46 is between 0.80 and 0.93 inch, with approximately 0.803 to 0.924 inch being preferred. Another preferred dimension of the bag 10 is that a distance "T" between the transverse segment 70 to an edge 72 of the outlet seal 44, which is represented by a sealed web, is approximately 0.803 inch. As is the case with the other listed dimensions, variations are contemplated depending on the application.

It will be seen that the reinforcing rib 68 generally corresponds to an approximate 90° angle α formed by the first outlet end seal 54, and that the angled portion of the outlet end seal is located between the reinforcing rib 68 and the tubular administrative outlet 38. Still another desired location of the dimple 50 is between the angle α and the inlet 40.

Figure 5:
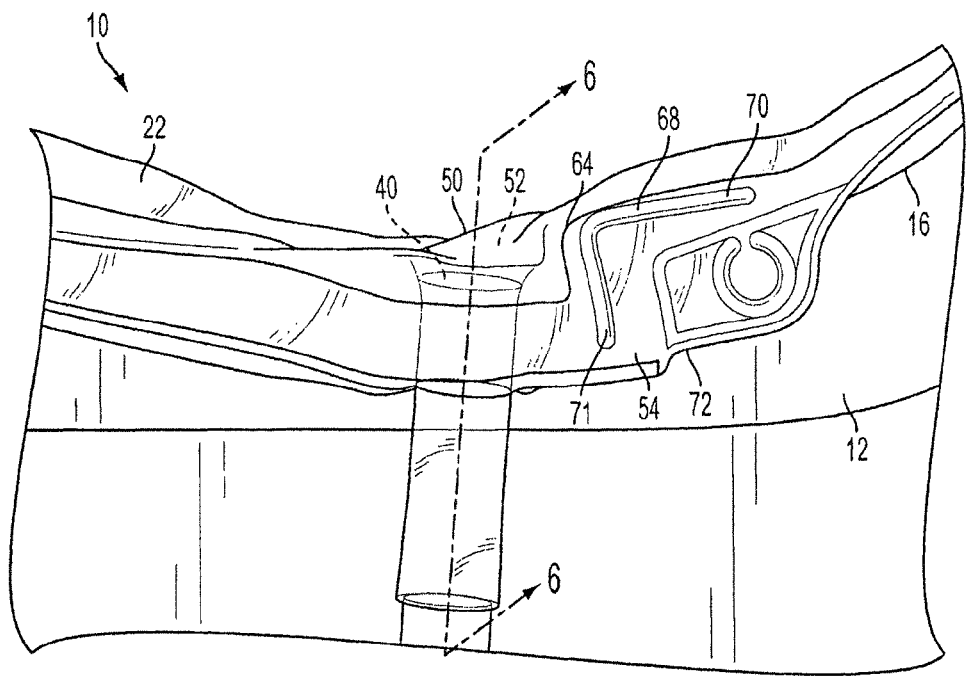
FIG. 5 is a fragmentary outlet end view of the present bag shown almost empty with the present dimple creating a space above the outlet tube inlet.
Figure 6:
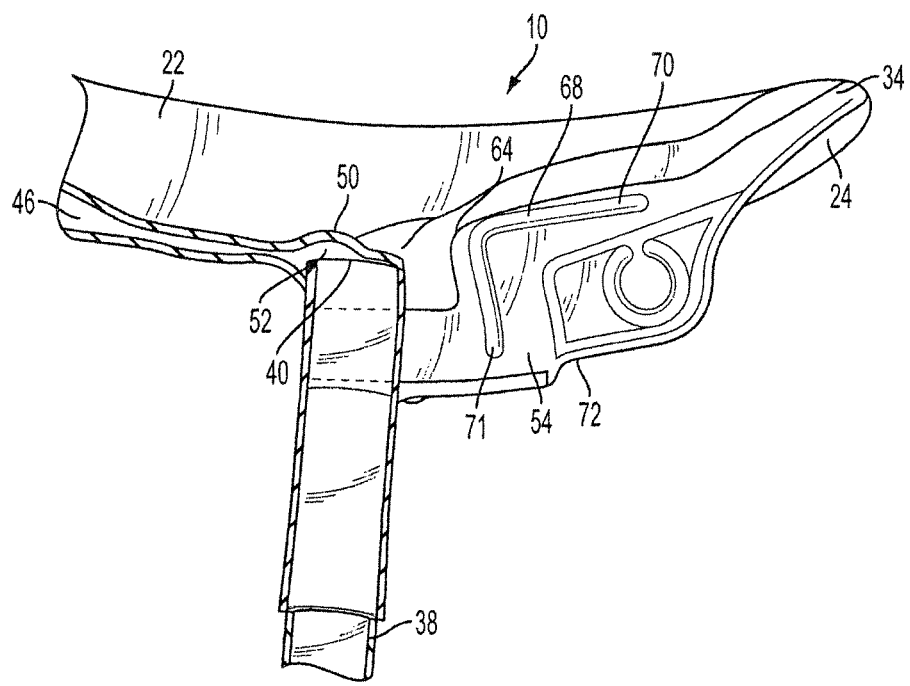
FIG. 6 is a cross-section taken along the line 6-6 of FIG. 5 and in the direction generally indicated.

Referring now to FIGS. 5 and 6, the dimple 50 is not always visible during the operational life of the bag 10, due in part to the stretching of the film layers 22, 24, during filling with the dialysis fluid, and the expected softening of the plastic layers as a result of the sterilization process. However, the above-identified structures combine to form the dimple 50 which is clearly present when the volume of dialysis fluid in the bag 10 is low enough that the upper and lower film layers 22, 24 touch each other in some regions of the bag. In addition, the structure of the present bag 10 is such that the dimple 50 is present and occlusion of the inlet 40 is prevented regardless of the orientation of the administrative outlet 38, either generally horizontal (FIG. 2), or generally vertical (FIG. 5) with respect to the APD cycler unit 12.

The present bag 10 was tested compared with a conventional bag similar to the bag 20 having a symmetrical outlet end seal, and lacking any sort of dimple. 503 conventional 6000 ml dialysis bags resulted in an alarm generation rate of 2.19%. A test group consisted of 503 of the present bags 20 having the dimple 50. The alarm generation rate for the test group was 0.199%. Thus, through testing (2.19−0.199)/2× 100=90.9%), it has been found that the use of the present bag 10 has resulted in a 90.0% reduction in occlusion related alarms.

In a second test, of 1153 6000 ml conventional dialysis bags lacking a dimple, an occlusion alarm was generated in 22 bags, for an alarm rate of 1.91%. In contrast, in a group of 1153 6000 ml bags having the present dimple, the occlusion alarm was generated in 0 bags.

As such, the present dialysis bag 10 featuring the dimple 50 has been shown to significantly prevent occlusion of the inlet 40 of the tubular administrative inlet 38. By creating an air space above the inlet 40 as the bag empties, the adjacent film layer 22 is prevented from collapsing upon the inlet. As such occlusion alarms are significantly reduced, compared to conventional dialysis bags.

While a particular embodiment of the present dialysis bag with anti-occlusion feature has been shown and described, it will be appreciated by those skilled in the art that changes and modifications may be made thereto without departing from the invention in its broader aspects and as set forth in the following claims.

What is claimed:

1. A dialysis bag, comprising: a first layer of film and a second layer of film each having a closed end and an opposite outlet end; said layers sealed together about corresponding peripheral edges to define a bag chamber; an outlet assembly sealingly disposed at said corresponding outlet ends and having a tubular administrative outlet with an inlet and being in fluid communication with said bag chamber, said outlet being sealingly sandwiched between said first and second layers of film and said inlet projecting past a seal joining said layers and into said bag chamber; a dimple formed in said first layer adjacent to said inlet for preventing occlusion as a fluid level in said bag decreases; and a first outlet end seal connecting said first and second layers and having an axially extending segment being in spaced, parallel relationship to said administrative outlet, having a length extending linearly from said outlet end and having a seal segment end of said length extending farther axially into said bag chamber than said inlet, said dimple having a length and a width, said length being longer than said width and extending only along a line between said inlet and said seal segment end, with a first end of said dimple disposed adjacent said inlet, and a second end of said dimple being disposed adjacent said seal segment end.

2. The bag of claim 1 further including an outlet end seal securing said first and second layers at said outlet end on sides of said outlet assembly, forming a first outlet end seal and a second outlet end seal, said first outlet end seal being asymmetric with said second outlet end seal.

3. The bag of claim 2 wherein said first outlet end seal is provided with a reinforcing rib.

4. The bag of claim 2 wherein said tubular administrative outlet is laterally spaced from said first outlet end seal for enhancing formation of said dimple.

5. The bag of claim 4 wherein said outlet is spaced from said first outlet end seal between 1/16 and 5/16 inch.

6. The bag of claim 3 wherein said reinforcing rib is generally "L"-shaped.

7. The bag of claim 2 wherein said first outlet side seal has an angled portion forming an approximate 90 degree angle.

8. The bag of claim 7 further including a generally "L"-shaped reinforcing rib disposed on said first outlet side seal such that said angled portion is between said reinforcing rib and said tubular administrative outlet.

9. The bag of claim 1, wherein said first outlet end seal defines an angle, and said dimple extends between said angle and said inlet.

10. The bag of claim 9, wherein said angle includes a first portion extending generally parallel to an axis of said tubular administrative outlet, and a second portion extending generally transversely to said axis.

11. The bag of claim 10, wherein said second portion is spaced from an outlet edge of said first and second layers by a sealed web extending approximately 0.803 inch.

12. A peritoneal dialysis bag, comprising: a bag chamber defined by a pair of complementary layers sealed together to form a bag chamber therebetween and having a first, outlet end and a second, closed end opposite said outlet end; said bag layers sealed together in part at said outlet end by a first outlet end seal; at least one tubular administrative outlet sealingly disposed at said outlet end and in fluid communication with said bag chamber, said outlet having an inlet projecting into said bag chamber past a seal joining said bag layers together; said seal including a linear, axially extending seal segment extending in spaced, parallel relation to said outlet and into said bag chamber to create a displacement between an end of said segment and said inlet; and a dimple formed in at least one said layer, having a length and a width, the length being longer than said width and, said dimple having a first end adjacent said inlet of said outlet and a second end adjacent said end of said seal segment of said first outlet end seal for preventing occlusion of said inlet as said bag is depleted of fluid, said dimple located only along a line extending between said inlet and said end of said segment.

13. The bag of claim 12, wherein said dimple is constructed and arranged so that occlusion is prevented regardless of the angular orientation of said tubular administrative outlet relative to said bag.

14. The bag of claim 12, wherein said dimple is formed in part by said first outlet seal being asymmetrical with a second outlet seal, and said tubular inlet is closer to said first outlet seal than to said second outlet seal.

15. The bag of claim 12, wherein said first outlet seal includes a second seal segment that defines an angle with said portion extending generally parallel to an axis defined by said tubular inlet, and said second seal segment is spaced between 3/16 and 9/16 inch from said inlet of said outlet.

16. The bag of claim 14, further including a generally "L"-shaped support rib disposed relative to said first outlet seal such that said seal portion is located between said rib and said tubular administrative outlet.

17. A peritoneal dialysis bag, comprising: at least one tubular administrative outlet sealingly disposed at an outlet end of a bag chamber and in fluid communication with said bag chamber, said outlet having an inlet projecting into said bag chamber past a seal joining said bag layers together; a dimple formed in at least one said bag layer and having a first end adjacent said inlet and a second end adjacent an end of an axially extending segment of a first outlet end seal, wherein said dimple extends only along a line between said inlet and said seal segment end, said first outlet end seal being asymmetrical with a second outlet end seal, said axially extending segment of said first outlet end seal extending further axially into said bag chamber than said inlet of said first outlet end seal and also further axially relative to said second outlet end seal; said inlet is closer to said first outlet end seal than to said second outlet end seal; and a generally "L"-shaped support rib being disposed relative to said first outlet end seal such that said seal portion is located between said rib and said tubular administrative outlet.

* * * * *